United States Patent [19]

Herrala et al.

[11] Patent Number: 5,381,341
[45] Date of Patent: Jan. 10, 1995

[54] CONTROL SYSTEM FOR A PAPER OR BOARD MACHINE

[75] Inventors: Juha Herrala; Jouko Hytönen, both of Jyväskylä; Jarmo Järvinen, Jyskä; Markku Salmela, Keski-Palokka; Harri Vähätalo, Jyväskylä, all of Finland

[73] Assignee: Valmet Paper Machinery Incorporated, Helsinki, Finland

[21] Appl. No.: 20,251

[22] Filed: Feb. 18, 1993

Related U.S. Application Data

[63] Continuation of Ser. No. 531,877, Jun. 1, 1990, abandoned.

[30] Foreign Application Priority Data

Jun. 1, 1989 [FI] Finland ................... 892670

[51] Int. Cl.⁶ ........................ G06F 15/46; D21F 1/02
[52] U.S. Cl. ...................... 364/471; 162/252; 162/253; 162/262
[58] Field of Search ................... 364/469, 471, 132; 162/252, 253, 262, 263, 256, 257, 258, DIG. 10

[56] References Cited

U.S. PATENT DOCUMENTS

| | | |
|---|---|---|
| 3,666,621 | 5/1972 | Adams . |
| 4,374,703 | 2/1983 | Lebeau et al. ............. 364/471 |
| 4,500,968 | 2/1985 | Blalkowski ................. 364/471 |
| 4,578,764 | 3/1986 | Hutchins et al. ........... 364/131 |
| 4,626,984 | 12/1986 | Unruh et al. ............... 364/132 |
| 4,680,089 | 7/1987 | Aral et al. .................. 364/471 |
| 4,707,779 | 11/1987 | Hu ............................... 364/471 |
| 4,745,744 | 5/1988 | Cherry et al. .............. 364/132 |
| 4,748,400 | 5/1988 | Typpo ............................ 73/74 |
| 4,947,684 | 9/1990 | Balakrishnan ............. 364/471 |
| 4,957,770 | 9/1990 | Howarth ..................... 162/265 |

FOREIGN PATENT DOCUMENTS

| | | |
|---|---|---|
| 0041486A1 | 5/1981 | European Pat. Off. ....... D21F 1/02 |
| 8228998 | 10/1982 | United Kingdom . |
| 8303614 | 2/1983 | United Kingdom . |

OTHER PUBLICATIONS

Siler, Steven J., "Cross-machine basis-weight control: machine considerations", 872 Tappi Journal 67, No. 12 (Dec. 1984), pp. 52-55.

Primary Examiner—Roy N. Envall, Jr.
Assistant Examiner—Thomas E. Brown
Attorney, Agent, or Firm—Cohen, Pontani, Lieberman, Pavane

[57] ABSTRACT

A control system regulating the transverse profile of properties of a web in a paper or board machine is disclosed. The control system comprises a plurality of actuators and a corresponding plurality of actuator controllers. The actuators are arranged to be effective across the width of the web whose profile is to be regulated. Further included is a process controller and a feedback network connected to the process controller and provided with an arrangement for measuring the web profile to be regulated. The actuators are provided with intelligent actuator controllers. A data bus common to the actuator controllers is provided, along which occur data communications in a control hierarchy between a higher control device and said actuator controllers.

16 Claims, 5 Drawing Sheets

CONTROL SYSTEM FOR A PAPER OR BOARD MACHINE

This is a continuation, of U.S. application Ser. No. 07/531,877, filed Jun. 1, 1990, now abandoned.

BACKGROUND AND SUMMARY OF THE INVENTION

The invention concerns a control system for a paper or board machine, by means of which the transverse profile of properties of the web to be produced, in particular its thickness profile, is regulated. The control system, more particularly, comprises a number of actuators and a corresponding number of actuator controllers, said actuators being fitted to be effective across the width of the web whose profile is to be regulated, and said control system including a process computer of an equivalent logical component as well as a feedback branch provided with an arrangement for measurement of the web profile to be regulated.

As is known from prior art, a pulp suspension jet is fed out of the discharge opening in paper or board machines onto a forming wire or into the gap between forming wires. The transverse profile of the discharge opening of the headbox also determines the profile of the pulp jet. The profile of the discharge opening is regulated, and by means of this regulation it is also possible to compensate for any flaws in the pulp jet that have arisen in or before the headbox.

In the prior art, a control system for the grammage profile lip of the headbox of a paper machine is known, which system comprises an angle-gear/stepping motor control device, wherein the profile bar of the regulator lips is controlled by means of adjusting spindles attached to the profile bar at intervals of about 10 ... 15 cm, said spindles being displaced by stepping motors attached to their opposite ends by the intermediate of angle gears. The prior art control systems for adjusting spindles involve a number of drawbacks, most of which arise from the fact that the control of each actuator takes place separately directly from the system placed at a higher level in the hierarchy, which results, e.g., in the following drawbacks:

- the stepping motors are controlled in parallel, so that several wires are required for each individual actuator, because normally the number of actuators is about 50 to 100,
- as the actuators have no local intelligence, the control system placed higher in the hierarchy has to take care of the regulation of all of the actuators at the same time, which, of course, burdens said regulation system particularly heavily,
- owing to said burdening, the speed of the system also remains low and the response times become long,
- since all the actuators are regulated in the same way, local conditions and mechanical differences, e.g., in the angle gears, cannot be taken into account, so that the accuracy of regulation is deficient and detecting of erroneous operations is difficult.

As has come out above at least partly, by means of the prior art technology, the profiling of the profile bar of the discharge opening of the headbox takes place by separate control of each regulation gear by means of handling sequences carried out one after the other. In order that the positioning should be successful with the required accuracy of about 10 $\mu$m, electronics that measure the locations of the adjusting spindles are also required. Typically, the positioning takes place for about 5 seconds per actuator, and the reading of measurement alone takes 1.2 seconds. Thus, running through all of the actuators on a profile bar with 80 adjusting spindles takes from 1.5 to 6.5 minutes. Information is obtained on the state of an actuator momentarily only.

As is known in the prior art, the systems of cables from the processor cabinet are arranged by means of two system cables and electricity supply cables from the dry spaces to the wiring cabinet placed at the headbox (distance 50 to 250 meters), from where separate candles are passed to the location detector and stepping motor of each actuator (10 to 30 meters).

In paper and board machines and in related size presses, coating devices and calenders, the profile of the web that is being produced is regulated by means of devices in which, at least partly, the same problems are present as in the above prior-art systems for the regulation of the profile of the discharge opening of the headbox. Thus, the present invention is not confined to a control system for the discharge opening of a headbox alone, but it can be applied in various regulation devices for paper and board machines as well as for their finishing equipment by means of which devices the transverse profile of properties of the web is controlled. In addition to the devices mentioned above, further prior-art devices that affect the transverse profile of the web are, for example, steam boxes fitted in the press section of a paper machine, devices for profiling of the coating blades in a coating machine, as well as electric induction heating devices fitted, e.g., in connection with calender rolls, by means of which heating devices the profile of linear loads in a calendering nip is controlled.

In view of achieving the objectives stated above and those that will come out later, the invention is mainly characterized in that the various actuators in the control system are provided with intelligent actuator controllers and that the data communications in the control hierarchy between a higher control device and the various actuator controllers are arranged along a bus common of the various actuator controllers.

In the control system in accordance with the invention, the regulation is based on decentralized intelligence of actuators, which is just parametered by the higher system by giving the set values. Each actuator controller is seen upwards as an independent unit, to which a set value is given in digital form along the serial bus, whereupon the actuator controller handles the mechanical regulation independently in accordance with its own measurement-regulation algorithm.

The controlling apparatus placed at a higher level in the control hierarchy may be a bus server specifically provided for this purpose, said server transferring set values from the automation system to the actuators and status and measurement values from the actuator towards the system. The automation system may also control the actuators directly based on a certain line discipline.

The bus between the automation system and the series of actuators may consist of a simple asynchronous line. Thus, one cable only is required to pass to the entire series of actuators. Moreover, operating electricity is needed for the control card and for the stepping motors.

Having transmitted the set values to the actuators, the system at the higher level is free from load; the regulation/measurement takes place in the actuators independently and simultaneously. Thus, the regulation does not load the system, and the speed of operation is substantially higher than in the prior art.

In the invention, each individual actuator that regulates the transverse profile of the web is arranged as an independent positioning device, which is, when necessary, capable of monitoring its own operation in real time. The actuators are connected to the system for the calculation of profiling by means of a serial bus, whereby the amount of operations taking place at the same time is limited by the data transfer speed or by the capacity of the power source only. In the invention, if a data transfer speed of, e.g., 19,200 bauds is used for the control of the 80 spindles in the headbox while the message length is 8+6 bytes, for every actuator a new set value is obtained in less than two seconds. If it is desired to carry out the invention so that only ten (10) actuators are operative at one time, the positioning of all of the actuators takes less than half a minute.

In the invention, the system of cables between the control system and the series of actuators can be accomplished by means of a comb-like voltage and data distribution chain, to which the actuator controllers themselves are connected in direct proximity of the actuator, which consists, e.g., of a gear, a position detector, and of a motor.

The electronic systems of the actuators can be accomplished as standard modules, which are identical in the case of each actuator. In connection with the installation, each device can be given its own code by means of rotating switches provided on a card, whereupon the device can operate correctly in the bus when it recognizes its own code. Thus, the higher controlling system transmits set values for all the actuators through the bus, and it can read the measurement value as well as the status, which contains status and error data.

The electronics card of each individual actuator has preferably its own processor, memory, serial-communication electronics, integrated control electronics for the stepping motor, and an A/D-converter for carrying out the measurement from a LVDT-detector. The software contained in the card handles the serial communications upwards, the control of the stepping motor on the basis of the set values given, and the feedback measurement regarding the completion of the adjustment. During running, if necessary, it is possible to examine, e.g., the operating temperature, the stiffness of the transmission system, the accuracy of the regulation, etc., quantities in whose values a substantial change causes an error message and discontinuation of the regulation. A quantity that is changed within normal limits is compensated for by, on the basis of an algorithm, calculating a suitable correction for the regulation or measurement.

The fact that the control and the diagnostics are based on software makes the device easily adaptable to different purposes of use and to different environments and even to control mechanics of a different type. Later fine tuning and improved algorithms can also be integrated in the device without difficulty.

BRIEF DESCRIPTION OF THE DRAWINGS

In the following, the invention and the prior art most closely related to same will be described in detail with reference to the figures in the accompanying drawing and to some advantageous exemplifying embodiments of the invention illustrated in said figures. In the drawings.

DETAILED DESCRIPTION OF THE PREFERRED EMBODIMENT

Figure 1:
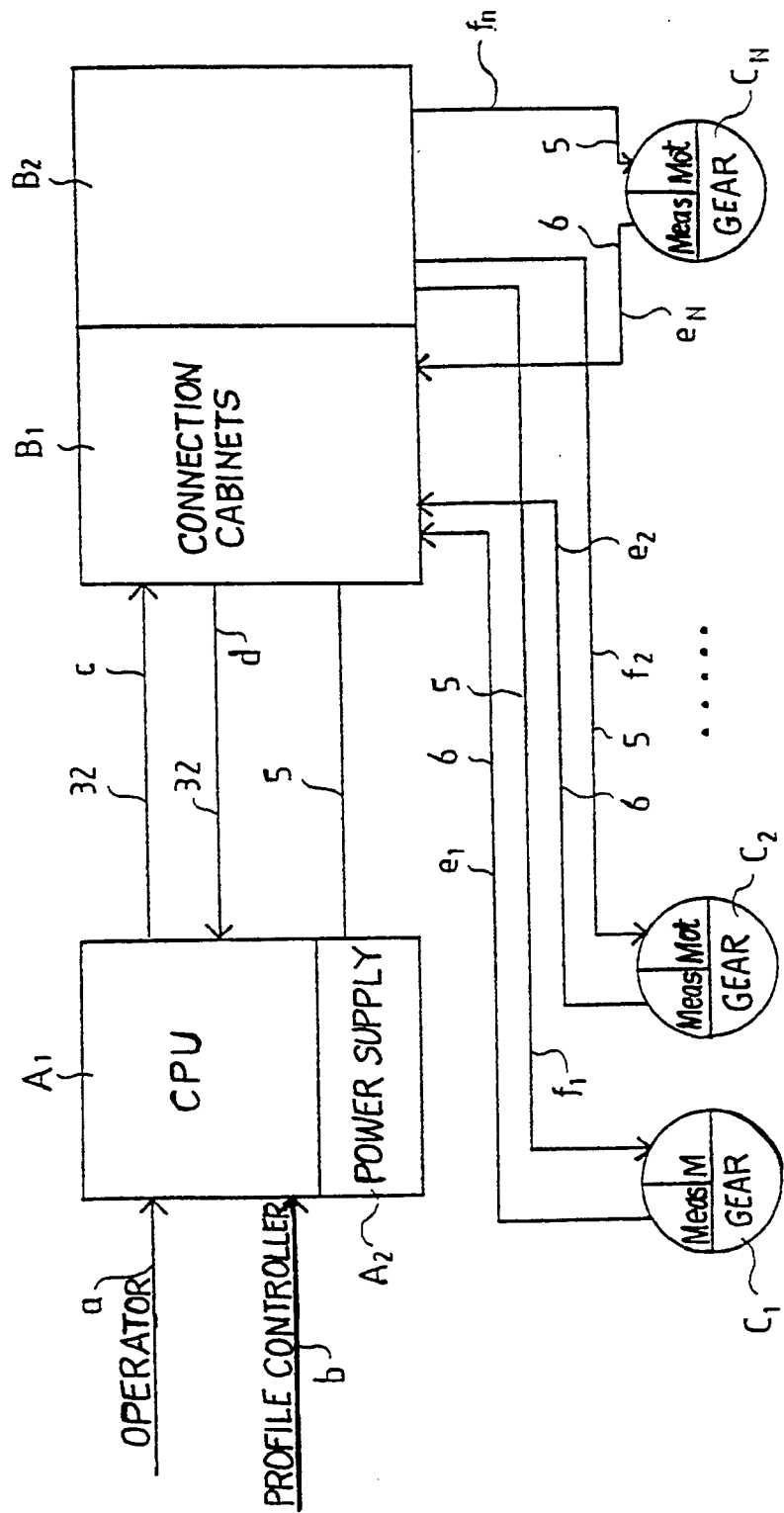
FIG. 1 illustrates the prior art that constitutes the starting point of the invention, in respect of the regulation of the discharge opening of a headbox.

FIG. 1 shows a prior art profile regulation system for the discharge opening of the headbox of a paper machine. The system comprises N pcs. of measurement-stepping-motor units $C_1 \ldots C_N$ placed side by side, by means of which units the adjusting spindles (FIG. 3, parts $31_1 \ldots 31_3$), which are connected to the profile bar that profiles the discharge opening, are regulated and measured. The control message is passed into each unit $C_1 \ldots C_N$ from the wiring cabinet $B_2$ through 6-pole separate cables $f_1 \ldots f_N$ and, in a corresponding way, the measurement messages of the units $C_1 \ldots C_N$ are transferred to the measurement unit $B_1$ placed in connection with the wiring cabinet $B_2$ from each unit by means of its own 5-pole cable $e_1 \ldots e_N$. The prior art control system comprises a central unit (CPU) $A_1$ and a source $A_2$ of electric power. The central unit $A_1$ receives the signals from the operation and maintenance station through the cable a, and the data on the profile of the paper web through the cable b. Between the central unit $A_1$ and the wiring cabinet $B_1$ there are two 32-pole cables c and d. This prior-art control system involves the drawbacks discussed above, which drawbacks are eliminated efficiently by the present invention.

Figure 2:
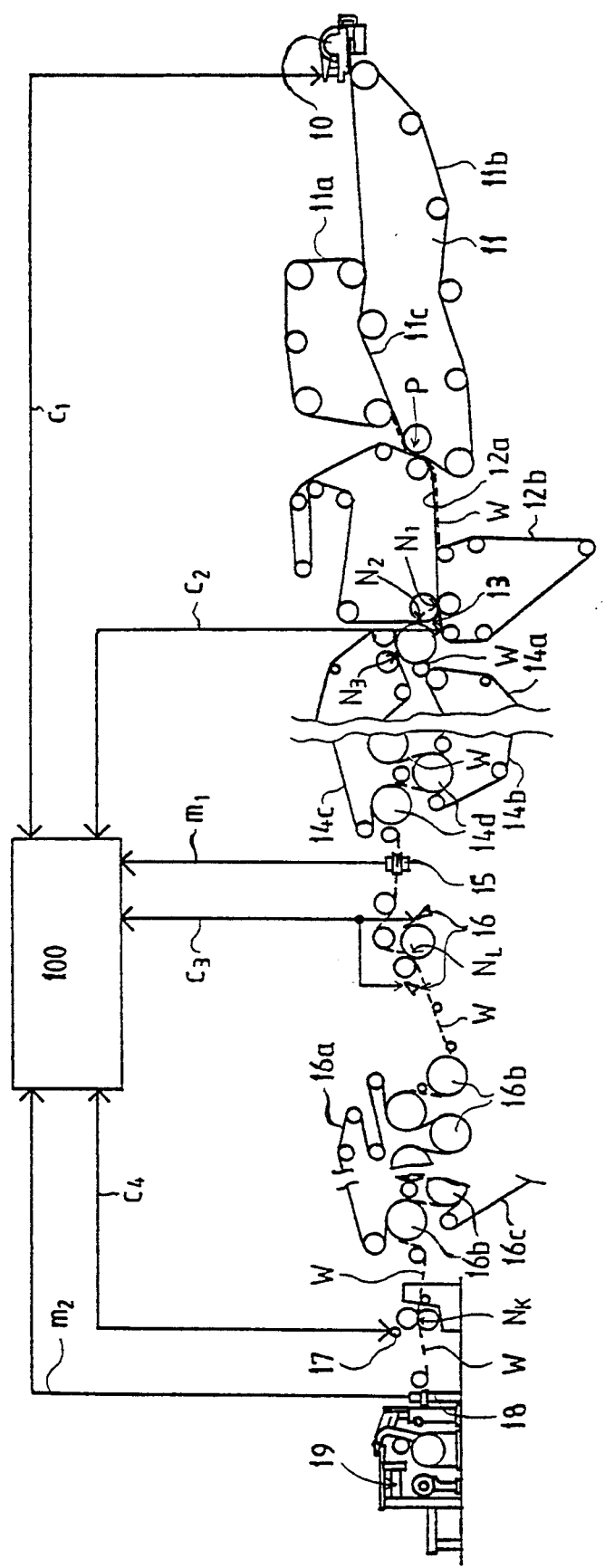
FIG. 2 is a schematical illustration of a paper machine and of related finishing equipment, in connection with which a control system and a series of actuator controllers in accordance with the invention are applied.

FIG. 2 illustrates various objects of application of the control system and actuator controller in accordance with the invention in paper or board machines and in related on-line finishing equipment. FIG. 2 is a schematical presentation of just one exemplifying embodiment of a paper machine, and the invention is in no way confined to said example, but it may be applied to a number of different paper or board machines wherein it is necessary to regulate the transverse profile of properties of the web that is being produced, in particular its thickness profile but, if necessary, also other profiles of properties, such as smoothness profile.

The paper machine shown in FIG. 2 includes a wire part 11, which consists of an upper wire 11a and of a lower wire 11b. The headbox 10 feeds a pulp suspension jet, whose transverse profile is controlled in accordance with the invention, onto the initial part of the lower wire. Hereupon there follows a twin-wire portion 11c. From the lower wire 11b the web is detached at the pick-up point P, being transferred into the press section onto the upper felt 12a, on whose lower face the web W is passed into the first nip $N_1$ in the press section, said nip being a two-felt 12a,12b nip. After the first nip $N_1$ the web W follows the upper felt 12a and is transferred into the second nip $N_2$, from which the web W is transferred on the smooth face of the center roll in the press into the third nip $N_3$, and from it further onto the fourth felt 14a in the press.

FIG. 2 shows, of the end portion of the pre-dryer, the upper drying wire 14c and the lower drying wire 14b as well as the last drying cylinders 14d. The dryer is followed by an on-line coating device, which is provided with blade coaters 16 and with a coating nip $N_L$, after which the web W is transferred into an after-dryer, which comprises drying cylinders 16b and a drying wire 16a. FIG. 1 shows the last drying cylinders 16b and the lower wire 16c of the after-dryer, after which the web W passes through a calendering nip $N_K$ and from there further onto the Pope-type reel-up 19.

As is shown in FIG. 2, the control system 100 in accordance with the invention and the related actuator controllers are applied to profiling of the discharge opening in a headbox 10, to control of the adjusting spindles of the steam box 13 placed between the press nips $N_1$ and $N_2$ in connection with the suction roll, to profiling of the coating blade in the blade coater 16, and/or to profiling of the calendering nip $N_K$ by means of inductive heating devices 17. As is shown in FIG. 2, the control system 100 is provided with a feedback branch, wherein the properties of the web W, e.g. its transverse thickness profile, are measured by means of a traversing measurement detector 15 or a corresponding series of detectors, placed after the drying section, and by means of a corresponding measurement beam 18 fitted after the calender, in connection with which beam there may also be measurement of the transverse smoothness profile or equivalent of the web W.

In operation, the heat profiling device 17 heats the roll of the calendering nip $N_K$, and the distribution of the heating effect of the device 17 in the cross-machine or transverse direction, i.e. in the axial direction of the calendering rolls, is controllable. When the distribution of the radius of the upper calendering roll of the nip $N_K$ changes because of the profiled heating of that roll, the distribution of the nip pressure in the calendering nip $N_K$ also changes, thereby enabling the web to be profiled in the cross-machine direction.

Said web profile measurement devices 15 and 18 are connected to the control system 100 by means of the connections $m_1$ and $m_2$. The control system 100 controls the series of the various actuators through the connections $c_1, c_2, c_3$ and $c_4$, said series comprising the actuator controllers in accordance with the present invention, which will be described later. The data on the positions and status of the various actuators are also transferred through the connections $c_1, c_2, c_3$ and $c_4$ to the control system 100.

It should be stated that, in FIG. 2, the control system 100 and the paper machine are shown highly schematically, and FIG. 2 is just intended to illustrate various fields of application of the invention wherein a transverse profile of properties of the web W to be produced is regulated.

Figure 3:
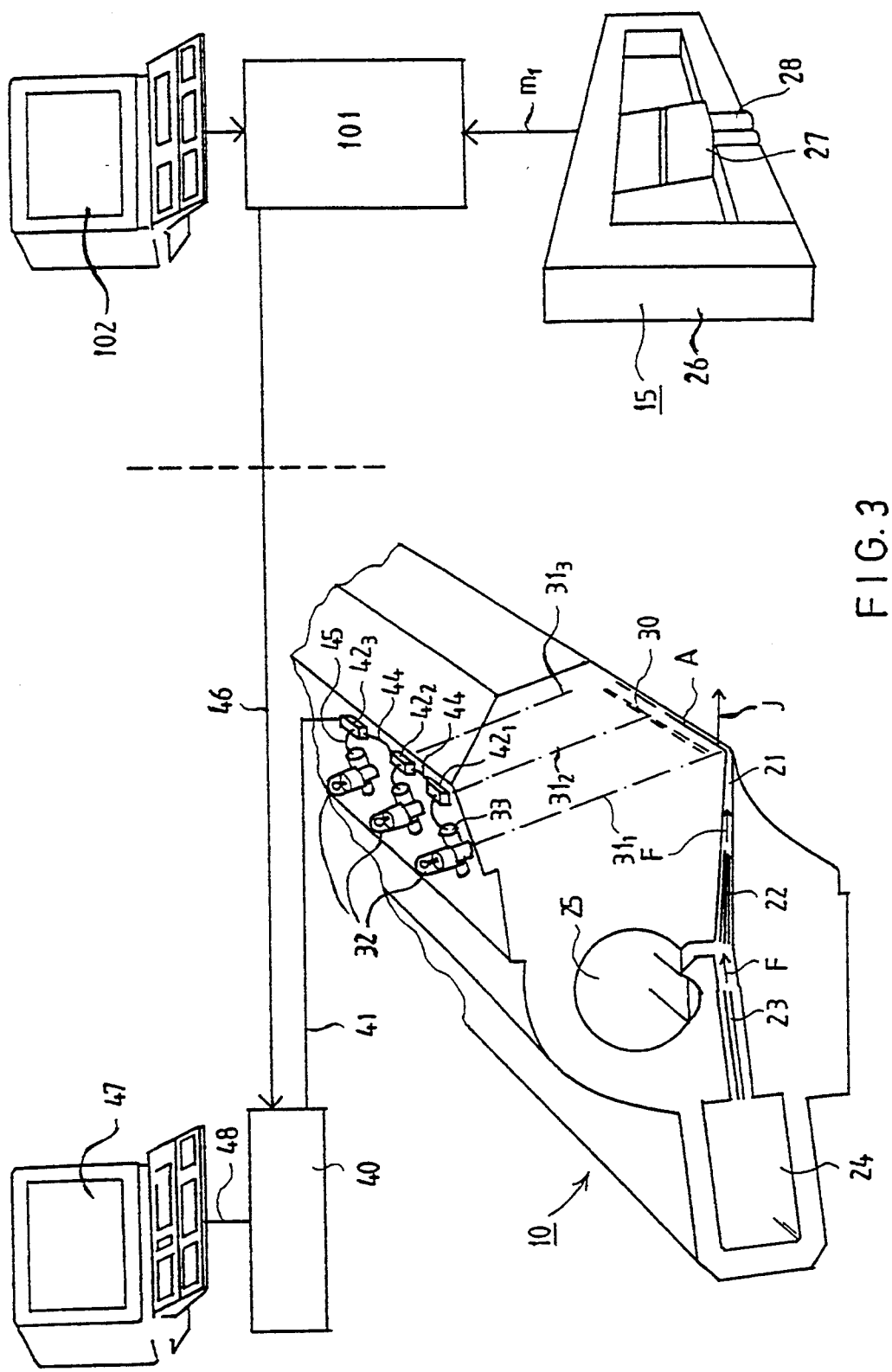
FIG. 3 is a schematical and partly axonometric view of a control system in accordance with the invention as applied to the regulation of the discharge opening of the headbox of a paper machine.

FIG. 3 is a more detailed illustration of an application of the invention to the regulation of the transverse profile of the pulp suspension jet J discharged out of the discharge opening A of the headbox 10 of a paper machine onto the forming wire 11b. Some details of the headbox 10 are known in the prior art. Starting from the discharge opening A and going in the direction opposite to the direction of flow F of the pulp suspension, the headbox 10 comprises first a discharge duct 21, then a turbulence generator 22, an equalizing chamber 25, a set of distribution tubes 23, and a distributor beam 24. To the front wall of the upper lip beam, in a way known in itself, the profile bar 30 is fixed, which determines the profile of the discharge opening A and thereby the transverse profile of the pulp jet.

Figure 4:
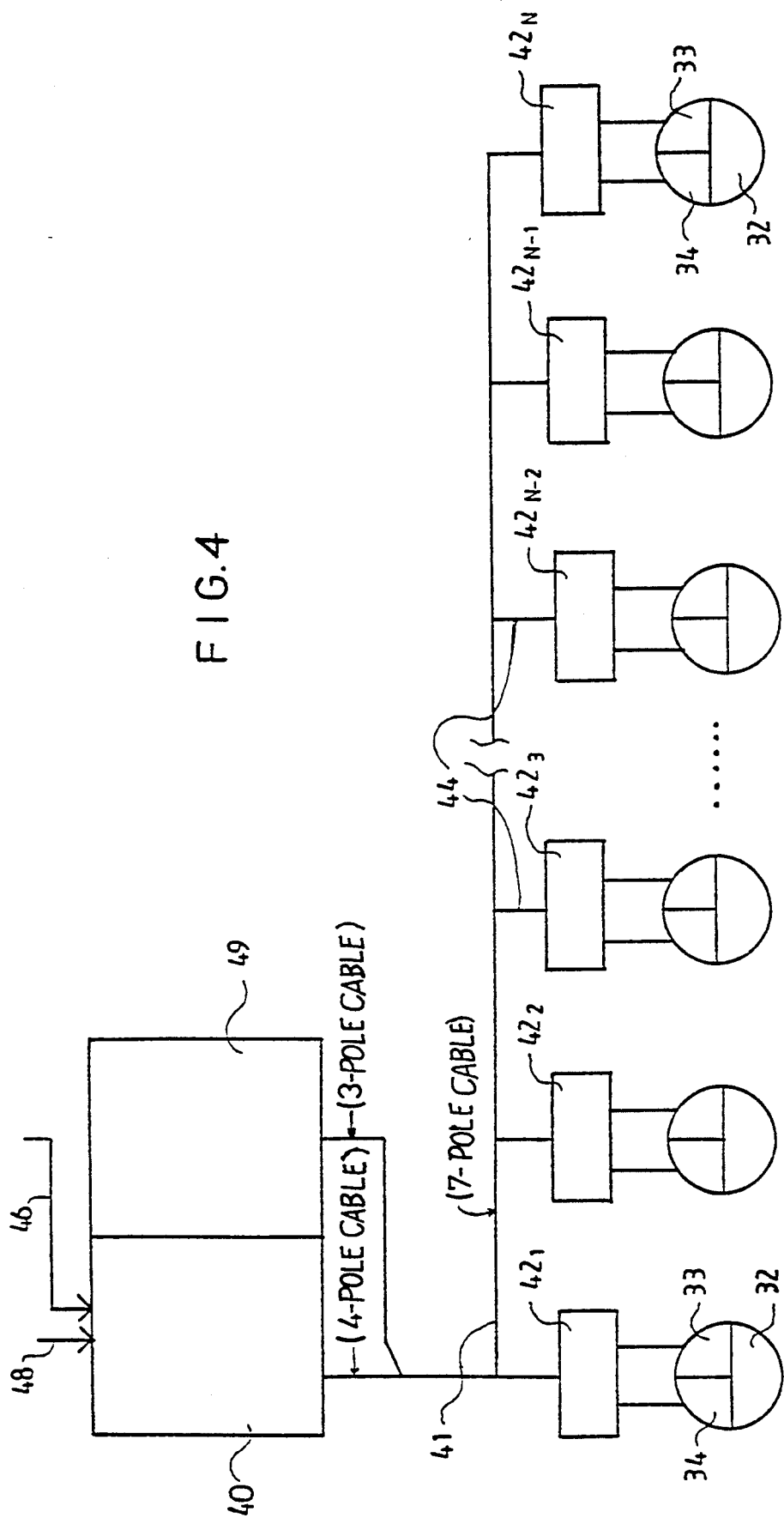
FIG. 4 shows the principle of realizing a control system and an actuator controller in accordance with the invention, in a way corresponding to FIG. 1.

The profile bar 30 is attached to adjusting spindles $31_1 \ldots 31_N$. If the spindles 31 are at distances of, e.g., 10 cm from one another, a paper machine of a width of about 8 m comprises 80 pcs. of adjusting spindles (N=80). Each adjusting spindle 31 is connected with an angle gear 32, by whose intermediate the stepping motors 33 displace the spindles 31 in their longitudinal direction. Each individual angle-gear/stepping-motor unit 32,33 is connected with an intelligent actuator controller $42_1 \ldots 42_N$ of its own by the intermediate of a cable 45. Said controllers $42_1 \ldots 42_N$ are identical with one another, and an advantageous exemplifying embodiment thereof will be described in more detail later, in particular with reference to FIGS. 4 and 5.

The individual actuator controllers 42 are connected to a common cable 41, which has a part 44 with rake-like division. The cable 41 is an, e.g., 7-pole cable, and it has four poles connected to the network server 40 and three poles connected to the source 49 (FIG. 4) of electric power. The controller parts 42 are connected to the measurement part 34 and to the stepping-motor part 33 by means of cables 45. The network server 40 receives the control signals through a cable 48 from the operator station 47 and, through cables 46, the control signals from the web W profile measurement and control computer 101.

FIG. 3 shows at the lower right a web profile measurement station 15, in which, in connection with a system of measurement beams 26 and with a carriage 28 moving on said system of beams, there is a web profile measurement detector 27, from which the measurement signal $m_1$ is obtained. Said measurement signal $m_1$ is passed to the measurement and control computer 101, whose operation and maintenance station is denoted with the reference numeral 102. From the computer 101, the profile control data are fed through the cable 46 to the network server 40.

According to the present invention, the intelligent actuator controllers 42, which are preferably identical with each other and whose number is N pcs. (as a rule, N=10 ... 100), operate, each of them, as independent positioning devices, which also monitor their own operations in real time. The cable 41 and its rake part 44 form a part of the serial bus so that the amount of simultaneous operations is limited by the speed of data transfer or by the capacity of the power source only. When a data transfer speed of 19,200 bauds is used and when the message length is 8+6 bytes, a new set value is obtained for each controller 42, when the number of spindles 31 is N=80, in a time shorter than 2 s.

Figure 5:
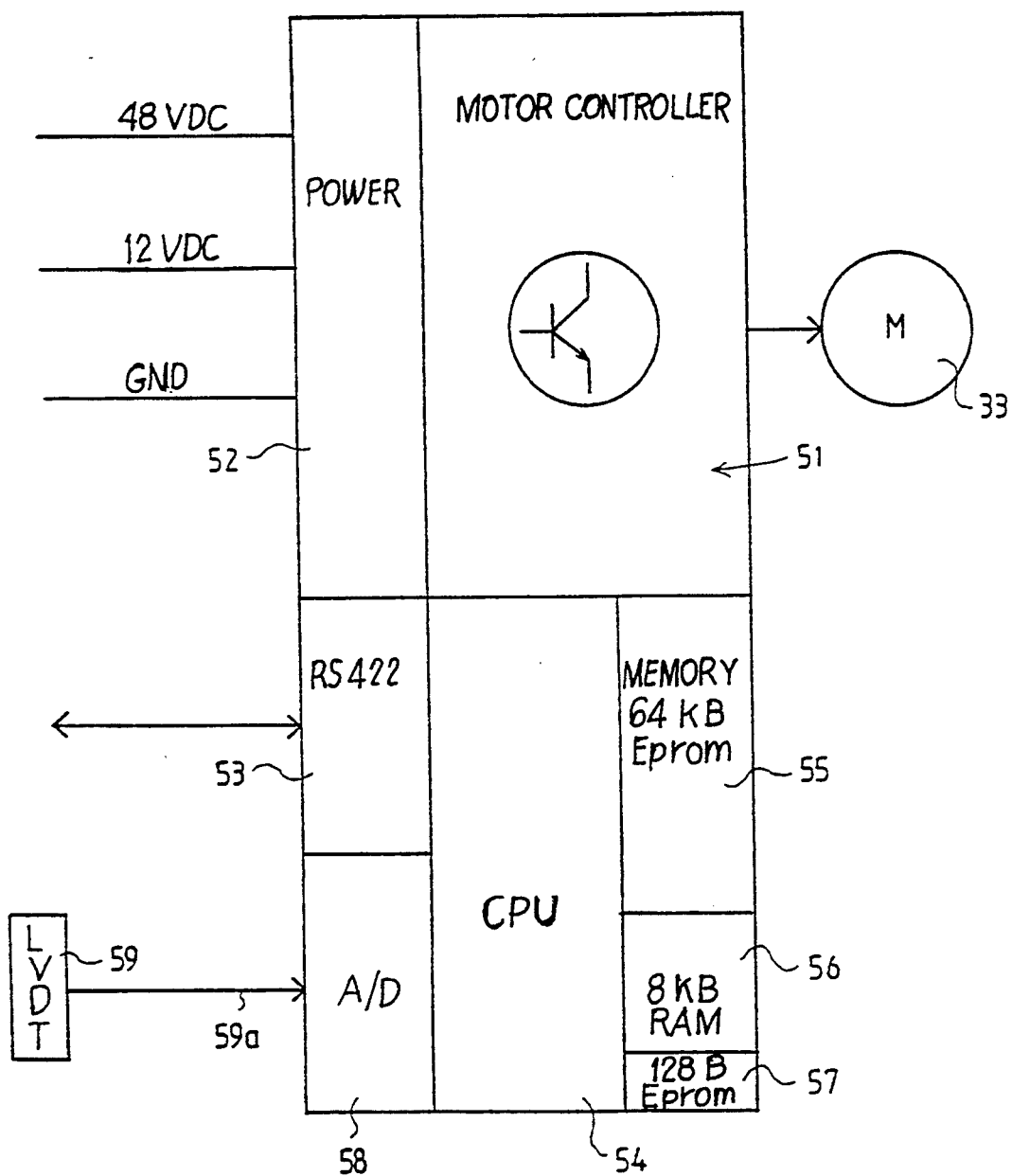
FIG. 5 shows a block diagram of an actuator controller.

According to FIG. 5, the electronic system of each operator controller 42 consists of five operational sections, which are: measurement part 58,59,59a; control part 51; current source 52; processor part 54,55,56,57, and a switchboard panel.

For the measurement of the movements of the lower ends of the spindles $31_1 \ldots 31_N$, LVDT-detectors 59 are used, to whose primary winding a suitable AC-voltage is supplied. Operation amplifier rectifiers placed in the secondary windings of the detectors 59 rectify the AC-voltages, which are obtained from the winding halves and which are proportional to the movement of the spindle 31. The output voltage is measured by means of an A/D-converter 58, and the processor unit 54 reads the A/D-converter 58 through a synchronous serial bus made of I/O-gates and places the conversion result obtained in the RAM 56.

The control electronics of the stepping motor 33 consist of power transistors, return diodes being connected in parallel with said transistors. The current passing through the stepping motor 33 is stabilized by means of comparators, which cut the control of the power transistors when the current in the stepping motor becomes excessively high. The controls proper of the power transistors are obtained, as optoisolated, from the gates of the CPU 54.

The processor part 54 . . . 57 consists, e.g., of an Intel CPU 80C31, which in itself contains 15 I/O-gates, USART, as well as two 8-bit counters. The capacity of the program memory 55 is, e.g., 65 kB, and the capacity of data memory 56 is 8 kB as a battery-powered RAM and 128 bytes as an EEPROM 52. In the EEPROM 57, the scaling coefficient of the measurement as well as the operation point of the measurement are stored. The control of the stepping motor 33 is carried out by means of buffered and optically isolated I/O-gates. Upon switching on of the voltages, the effects of said controls are prevented until the reset of the CPU 54 is removed and the carrying out of the program is started. A "watchdog" feature monitors the operation of the programs and, in the first stage, resets the CPU 58 unless the program resets the watchdog to zero within 200 ms. The processor part also includes the transmitter-receivers of the connection 53, which adapt the $0-5V$ voltage level used by the USART of the CPU to the RS 422 standard.

The communications between the actuator controllers 42 and the network server 40 take place along the RS422 connection. It is electrically compatible also with a RS485 interface. The communications take place with 9 bits, so that, when the starting signal (STX) of a message is transmitted, the last bit to be transmitted is "1" but, when other signals of a message is transmitted, "0". All actuators that have activated the detection of the 9th bit in their USART receive the starting signal. Having received the starting signal, the actuators activate their USART to receive such signals whose last bit is "0", because all the subsequent bytes in a message will be transmitted so that the last bit to be transmitted is "0".

The communications between the network server 40 and the actuator controllers 42 take place with the question-reply principle, wherein the network server 40 acts as the master of the bus.

A message consists of a frame composed of a starting signal STX, an address ADDRESS, message type MESSAGE, message length LENGTH, a check sum BCC, as well as of an end signal ETX. The length of the address field in the frame is 8 bits, so that, at the maximum, 255 actuators can be connected to the network. The formats of the message data and frame are binary. Normally an actuator replies to a question message with a reply message except in situations of error, in which case the actuator transmits a reject message (NACK) to the service unit. Error situations identified by the actuator in the communications include:
incorrect message type
incorrect message length
incorrect check sum
time-out between signals has elapsed
end signal of message missing In the communications, an individual actuator controller 42 is referred to by means of an address, whereby the actuator replies to the message by means of a reply message. If a message is intended for all actuators connected to the bus, the contents of the address field of the message are 00H. The actuators do not give any received notice to a message intended to the address 00H, but they carry out the requested operation directly upon arrival of the message.

The network server 40 identifies the same error situations in message communications as the actuator does. Moreover, the network server 40 monitors the time taken between a question message and a reply message and, upon elapse of the time-out between messages (5 seconds), repeats the transmission of the message. The transmissions of renewal messages are repeated 5 times and, unless the actuator controller 42 replies, the service unit stops communicating with the actuator controller concerned. In an error situation, the above operation also takes place when the actuator controller 42 acknowledges a message transmitted to it by means of a reject message. In an error situation, the communications with other actuator controllers 42 are interrupted, at the maximum, for 25 seconds. The service unit reports a defective actuator to the process level in a higher-level error message.

The actuator controllers $42_1$ . . . $42_N$ communicate with the process computer/process station by the intermediate of the RS422-interface 53. By means of message communications taking place along the connection 53, the set values are transmitted to the actuator, said set values being 16-bit 2-complement numbers. The set values are given as $\mu m$, so that, within said number range, a control range of 65,536 $\mu m$ is obtained. The zero point of the set values is the center point of the measurement range of the LVDT-detectors, determined on mechanical resetting to zero of the discharge opening A.

The actuator controllers $42_1$ . . . $42_N$ measure the locations of the adjusting spindles $31_1$ . . . $31_N$ independently and monitor the rationality of the measurement values. In a situation of measurement error, the actuator judges the nature of the defect and, based on its seriousness, either just reports the defect or prohibits adjustment of the spindle 31 concerned by setting it in prohibition of adjustment. The measurement of location is carried out by means of a double-integrating A/D-converter, whose conversion cycle lasts about 200 ms. This is why, by means of the measurement, it is not possible to detect high-frequency oscillation in the location of the spindle 31.

The spindles $31_1$ . . . $31_N$ coupled with the angle gears 32 are adjusted by means of stepping motors 33, in which one adjustment step displaces the spindle 31 by about 1.2 $\mu m$. The running of the spindle 31 to a new set value takes place in four steps:
step 1: the play in the angle gear and the location of the spindle in relation to the play are measured,
step 2: the spindle is run to the calculated new set value; the play is taken into account when the running direction is changed,
step 3: checking measurement is carried out,
step 4: a correction run is carried out if necessary.

Owing to differences in tightness in angle gears 32, the spindles 31 do not necessarily reach the new set value with one attempt. The operator may determine the maximum number of attempts, after which the actuator 42 notifies of an adjustment error if the set value has not been reached.

On the basis of the number of attempts needed to reach a new set value, the actuator determines for itself a so-called control index number, by means of whose examination the service operator can judge the tightness of an angle gear.

The control output stage of the stepping motors is provided with a thermostat activated by an excessively high temperature in the output stage circuits, said thermostat preventing control of the stepping motors 33. The activation of the thermostat is reported by the actuator 42 to the process computer, which must take into account the prevention of adjustment in its deflection limit monitoring. If desired, the thermostat can be acknowledged and disregarded from the process station or from any other monitoring device. In a situation of control error, the actuator places itself in running prohibition, which can, however, be disregarded by the operator.

The actuators monitor their operations and report any errors in operation to the higher level of process control. If the defect is serious, the actuator switches the operating voltages off, in which case the actuator does not reply to the question messages from the network server 40.

It should be understood that the preferred embodiments and examples described are for illustrative purposes only and are not to be construed as limiting the scope of the present invention which is properly delineated only in the appended claims.

What is claimed is:

1. A control system for regulating a transverse profile of a web in a paper or board machine, having a sensor for detecting the web transverse property profile and producing feedback information, said control system comprising:
   a plurality of intelligent actuator controllers, each independently executing a predetermined control algorithm and being responsive to an actuator control parameter received as a set value controller signal from a control bus and producing an actuator control signal;
   a plurality of controllable displacement actuators arranged at profile adjustment points across the width of the web, each being responsive to said actuator control signal from a corresponding one of said plurality of intelligent actuator controllers, each of said plurality of controllable displacement actuators being effective to adjust a transverse property of the web at a corresponding profile adjustment point, said plurality of controllable displacement actuators together being effective to regulate the web transverse property profile,
   a process controller, having as an output said set value controller signal transmitted as said actuator control parameter for each intelligent actuator controller and receiving as an input the feedback information from the sensor;
   said data bus being common to said plurality of intelligent actuator controllers and being arranged for data communications between said process controller and said plurality of intelligent actuator controllers, said data bus comprising a serial bus, and said intelligent actuator controllers generating controller information; and
   a network server connected between said data bus and said process controller for transferring said set value controller signal from said process controller to said plurality of actuator controllers and for communicating said controller information from said intelligent actuator controllers to said process controller.

2. The control system according to claim 1, wherein each of said plurality of actuator controllers comprises a substantially identical electronic module.

3. The control system according to claim 1, wherein each of said intelligent actuator controllers comprises an electronic circuit having a processor, memory, serial communication port for communicating with said process controller, actuator control port for controlling said corresponding arc of said actuators, and converter for receiving the output of an actuator movement detector.

4. The control system according to claim 3, wherein said data bus comprises a serial bus and said memory stores a predetermined program for said processor for control of said serial communication port to control communications with said serial bus.

5. The control system according to claim 1, wherein said plurality of actuators comprise adjusting spindles of a profile bar of a headbox of a paper machine, each having an angle gear and a stepping motor.

6. The control system according to claim 1, wherein said plurality of actuators comprise coating blade actuators of a paper-web coating device.

7. The control system according to claim 1, wherein said plurality of actuators comprise steam box actuators fitted in proximity of the web.

8. The control system according to claim 1, wherein said plurality of actuators regulate a profile of linear loads in a press nip of a paper machine.

9. The control system according to claim 1, wherein said plurality of actuators regulate a profile of linear loads in a calendaring nip in an on-line calendar of a paper machine.

10. The control system according to claim 9, wherein said plurality of actuators comprise inductive profiling devices for controlling said profile of linear loads in said calendaring nip.

11. A method of controlling the transverse profile of a property of a web produced in a paper machine comprising the steps of:
   providing a plurality of actuators, each said actuator being located at a profile adjustment point spaced across the width of the web and being responsive to a control signal, each of said plurality of actuators being effective to adjust a transverse property of the web at said profile adjustment point, said plurality of controllable displacement actuators together being effective to regulate the web transverse property profile;
   providing a plurality of independent intelligent actuator controllers, for independently generating said control signal and transmitting it to a corresponding one of said actuators, based on control parameters received from a communication interface;
   providing a process controller, receiving feedback relating to a web property and providing said control parameters to a common communication medium to which aid communication interface is connected;
   controlling said actuators by means of said actuator controllers to regulate the property of the web;
   measuring the property of the web;

inputting the measured property of the web as feedback into said process controller;

calculating control parameters as a correction for at least one of said actuators based on the measured property;

transmitting the correction for said at least one of said actuators to said common communication medium along with address information;

receiving the correction through aid communication interface from said common communication medium in said actuator controllers responsive to the address information associated with said at least one of said-actuators; and controlling said at least one of said actuators with said associated one of said actuator controllers in accordance with the correction.

12. The method according to claim 11, wherein said actuators comprise stepping motors, comprising tile further step of:

regulating the function of said one of said actuators by said associated one of said actuator controllers by means of feedback received from a linear variable differential transformer displacement detector associated with said one of said actuator, to provide a closed loop servo-regulation of a stepping motor, to control displacement of said one of said actuators.

13. The method according to claim 11, comprising the further steps of:

storing a parameter in one of said actuation controllers relating to a response of an associated one of said actuators to said control signal;

and modifying said control signal produced in response to the correction based on said stored parameter.

14. The method according to claim 11, comprising tile further step of:

transmitting a reply from said one of said actuator controllers to said common communication medium after receiving address information to which said one of said actuator controllers is responsive.

15. A control system for regulating a transverse property profile of a web in a paper or board machine, having a sensor for detecting the web transverse property profile and producing feedback information, said control system comprising:

a plurality of intelligent actuator controllers, each executing a predetermined control algorithm and being responsive to an actuator control parameter received as a controller signal from a control bus and producing an actuator control signal;

a plurality of controllable displacement actuators arranged at profile adjustment points across the width of the web, each being responsive to said actuator control signal from a corresponding one of said plurality of intelligent actuator controllers, each of said plurality of controllable displacement actuators being effective to adjust a a transverse property of the web at a corresponding profile adjustment point, said plurality of controllable displacement actuators together being effective to regulate the web transverse property profile; and a process controller, having as an output said controller signal transmitted as said actuator control parameter for each intelligent actuator controller and receiving as an input the feedback information from the sensor, said data bus being common to said plurality of intelligent actuator controllers and being arranged for data communications between said process controller and said plurality of intelligent actuator controllers, each of said intelligent actuator controllers comprising an electronic circuit having a processor, memory, serial communication port for communicating with said process controller, actuator control port for controlling said corresponding arc of said actuators, and a converter for receiving the output of an actuator movement detector, each of said intelligent actuator controllers further comprising an input for receiving at least one parameter corresponding to a measurement selected from the group consisting of an operating temperature, a mechanical property and a precision adjustment, an error condition output indicative of a substantial change in at least one parameter outside a normal limit, and an output providing an actuator control signal to said corresponding one of said actuators, produced in accordance with an algorithm for calculating a correction, provided said at least one parameter is within a normal limit, and discontinuing said algorithm if said at least one parameter is not within a normal limit.

16. A method of controlling the transverse profile of a property of a web produced in a paper machine comprising the steps of:

providing a plurality of actuators, each said actuator having a stepping motor and a spindle and being located at a profile adjustment point spaced across the width of the web and being responsive to a control signal, each of said plurality of actuators being effective to adjust a transverse property of the web at said profile adjustment point, said plurality of controllable displacement actuators together being effective to regulate the web transverse property profile;

providing a plurality of intelligent actuator controllers, for generating said control signal and transmitting it to a corresponding one of said actuators, based on control parameters received from a communication interface;

providing a process controller, receiving feedback relating to a web property and providing said control parameters to a common communication medium to which aid communication interface is connected;

controlling said actuators by means of said actuator controllers to regulate the property of the web;

measuring the property of the web;

inputting the measured property of the web as feedback into said process controller;

calculating control parameters as a correction for at least one of said actuators based on the measured property;

transmitting the correction for said at least one of said actuators to said common communication medium along with address information;

receiving the correction through aid communication interface from said common communication medium in said actuator controllers responsive to the address information associated with said at least one of said actuators;

controlling said at least one of said actuators with said associated one of said actuator controllers in accordance with the correction;

measuring a dead band in which a rotation of the spindle produces an attenuated displacement response of said one of said actuators to a control signal, and a location of the spindle in the dead band;
calculating a necessary displacement of tile spindle to achieve a desired correction;
rotating the spindle in an amount corresponding to tile calculated displacement, compensating for the measured dead band when a direction of rotation of the spindle is changed;
measuring the actual response of said one of said actuators to the control signal; and
correcting the displacement of the spindle to achieve the desired correction.

* * * * *